(12) United States Patent
Li et al.

(10) Patent No.: US 6,307,068 B1
(45) Date of Patent: Oct. 23, 2001

(54) ARTEMISININ DERIVATIVES, METHOD FOR THE PREPARATION THEREOF AND PHARMACEUTICAL COMPOSITIONS CONTAINING THE SAME

(75) Inventors: Ying Li; Feng Shan, both of Shanghai; Jin Ming Wu, Jiangsu; Guangshao Wu, Shanghai; Jian Ding, Shanghai; Jianxian Han, Shanghai, all of (CN); Ghanem Atassi, Saint Cloud; Pierre Renard, Le Chesnay, both of (FR)

(73) Assignee: Adir et Compagnie, Courbevoie (FR)

( * ) Notice: Subject to any disclaimer, the term of this patent is extended or adjusted under 35 U.S.C. 154(b) by 0 days.

(21) Appl. No.: 09/719,767

(22) PCT Filed: Jun. 9, 1999

(86) PCT No.: PCT/FR99/01359

§ 371 Date: Dec. 14, 2000

§ 102(e) Date: Dec. 14, 2000

(87) PCT Pub. No.: WO99/65914

PCT Pub. Date: Dec. 23, 1999

(30) Foreign Application Priority Data

Jun. 17, 1998 (CN) .................................. 98114788

(51) Int. Cl.$^7$ ....................... C07D 493/18; A61K 31/357
(52) U.S. Cl. ......................... 549/348; 549/354; 514/450
(58) Field of Search .................... 549/348, 354; 514/450

(56) References Cited

U.S. PATENT DOCUMENTS 5,219,880  6/1993  Thornfeldt ........................ 514/450

FOREIGN PATENT DOCUMENTS 0 428 773  5/1991  (EP) .
96 34602  11/1996  (WO) .

97 01548  1/1997  (WO) .

OTHER PUBLICATIONS

Guo–Qiang Zheng, Planta Medica, vol., 60, No. 1, 1994 pp 54–47.
H.J. Woerbenbag et al., Journal of Natural Products, vol. 56, No. 6, 1993, pp 849–856.
A.C. Beekman et al., Phytotherapy Research, vol. 10, 1996, pp. 140–144.
A.C. Beekman et al., Journal of Natural Products, vol. 60, No. 4, 1997, pp 325–330.
Mankil Jung, Bioorganic & Medicinal Chemistry Letters, vol. 7, No. 8, 1997, pp. 1091–1094.

*Primary Examiner*—Ba K. Trinh
(74) *Attorney, Agent, or Firm*—The Firm of Hueschen & Sage; G. Patrick Sage

(57) ABSTRACT

The invention relates to compound of the general formula (I):

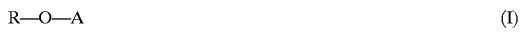

(I)

wherein:

R represents the radical of formula (II):

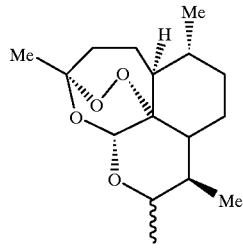

(II)

A is as defined in the description,
and medicinal products containing the same which are useful in treating or in preventing cancer.

14 Claims, No Drawings

ARTEMISININ DERIVATIVES, METHOD FOR THE PREPARATION THEREOF AND PHARMACEUTICAL COMPOSITIONS CONTAINING THE SAME

This application is a 371 of PCT/FR99/01359 dated Jun. 9, 1999.

FIELD OF THE INVENTION

The present invention relates to new artemisinine compounds having valuable pharmacological properties as antitumour agents.

BACKGROUND OF THE INVENTION AND DESCRIPTION OF THE PRIOR ART

Artemisinine is an active ingredient isolated from Artemisia annual. L., well known for its action against malaria.

A number of artemisinine compounds are described for their properties against malaria (IN 173339), in the treatment of toxoplasmosis (U.S. Pat. No. 5,486,535), or for their anti-cancer action, such as, for example, the dimers of artemisinine described in Application WO 9701548.

The compounds of the present invention are, by their novel structure, new and have especially valuable pharmacological properties as anti-tumour agents.

DETAILED DESCRIPTION OF THE INVENTION

More especially, the present invention relates to compounds of formula (I):

wherein:

R represents the radical of formula (II):

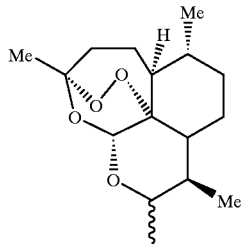

A represents:
a group of formula (III):

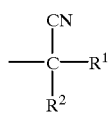

wherein—$R^1$ represents an aryl, substituted aryl, heteroaryl or substituted heteroaryl group, —$R^2$ represents a hydrogen atom or a substituted or unsubstituted linear or branched $(C_1-C_6)$alkyl group, or a group of formula (IV):

wherein—Y represents a substituted or unsubstituted linear or branched $(C_2-C_{14})$alkylene, substituted or unsubstituted linear or branched $(C_2-C_{14})$alkenylene, substituted or unsubstituted linear or branched $(C_2-C_{14})$alkynylene, phenylene, substituted phenylene, naphthylene or substituted naphthylene group, —Z represents an oxygen or sulphur atom, or a group $NR'^2$ wherein $R'^2$ can have the same meanings as $R^2$, —$R^3$ represents a group of formula (III) as defined hereinabove, it being understood that:

"aryl" is understood to mean a phenyl, naphthyl, phenanthryl, fluorenyl or anthryl group, "heteroaryl" is understood to mean any mono- or bi-cyclic aromatic group containing from 5 to 10 atoms and which may contain from 1 to 3 hetero atoms selected from oxygen, nitrogen and sulphur, the term "substituted" applied to the terms "aryl", "heteroaryl", "phenylene" and "naphthylene" means that those groups are substituted by one or more identical or different radicals selected from linear or branched $(C_1-C_6)$alkyl, hydroxy, linear or branched $(C_1-C_6)$alkoxy, $(C_1-C_6)$alkoxycarbonyl, polyhalo-$(C_1-C_6)$alkyl in which the alkyl moiety is linear or branched, aryloxy (unsubstituted or substituted by one or more identical or different groups selected from hydroxy, linear or branched $(C_1-C_6)$alkyl, linear or branched $(C_1-C_6)$-alkoxy, polyhalo-$(C_1-C_6)$alkyl in which the alkyl moiety is linear or branched and halogen atoms), nitro, amino, linear or branched $(C_1-C_6)$alkylamino, di-$(C_1-C_6)$alkylamino in which each alkyl moiety is linear or branched, alkylcarbonylamino, cyano and halogen atoms (fluorine, chlorine, bromine or iodine), or two adjacent carbon atoms may be substituted by an alkylenedioxy group, the term "substituted" applied to the terms "alkyl", "alkylene", "alkenylene" and "alkynylene" means that those groups are substituted by one or more identical or different radicals selected from hydroxy, linear or branched $(C_1-C_6)$alkoxy, polyhaloalkyl, amino and halogen atoms (fluorine, chlorine, bromine or iodine), their enantiomers and diastereoisomers, and addition salts thereof with a pharmaceutically acceptable acid or base.

Among the pharmaceutically acceptable acids there may be mentioned, in non-limiting manner, the following acids: hydrochloric, hydrobromic, sulphuric, phosphonic, acetic, trifluoroacetic, lactic, pyruvic, malonic, succinic, glutaric, fumaric, tartaric, maleic, citric, ascorbic, oxalic, methanesulphonic, camphoric, etc.

Among the pharmaceutically acceptable bases there may be mentioned, in non-limiting manner, sodium hydroxide, potassium hydroxide, triethylamine, tert-butylamine, etc.

The preferred compounds of the invention are those in which:

A represents a group of formula (III),

A represents a group of formula (IV),

Z represents an oxygen atom,

Z represents a group NR'$^2$,

Y represents a substituted or unsubstituted (C$_2$–C$_{14}$)-alkylene or -alkenylene chain, Y represents phenylene or naphthylene, each substituted or unsubstituted, R$^1$ represents an aryl or substituted aryl group.

Advantageously, the invention relates to compounds of formula (I) wherein A represents:

a group of formula (III) in which R$^1$ represents a substituted or unsubstituted phenyl group and R$^2$ represents a hydrogen atom or a methyl group, or a group of formula (IV) in which Y represents a —(CH$_2$)$_n$— chain wherein n is such that 2≦n≦7, Z represents an oxygen atom or a group NR'$^2$ and R$^3$ represents a group of formula (III) wherein R$^1$ represents a phenyl or naphthyl group, each substituted or unsubstituted, and R$^2$ represents a hydrogen atom or a methyl group.

More especially still, the invention relates to compounds of formula (I) which are:

2-(4-bromophenyl)-2-dihydroartemisininyl-acetonitrile, 2-phenyl-2-dihydroartemisininyl-acetonitrile,

[(2-chlorophenyl)(cyano)methyl]dihydroartemisininyl 1,4-succinate, dihydroartemisininyl 4-{[(4-bromophenyl)(cyano)methyl](methyl)amino}-4-oxobutanoate.

The enantiomers, diastereoisomers and addition salts with a pharmaceutically acceptable acid or base of the preferred compounds of the invention form an integral part of the invention.

The invention relates also to a process for the preparation of compounds of formula (I), characterised in that there is used as starting material a compound of formula (V):

R⌇OH      (V)

wherein R is as defined hereinabove, with which there is condensed under conditions of acid catalysis, a compound of formula (VI):

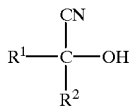
    (VI)

wherein R$^1$ and R$^2$ are as defined hereinabove, to yield a compound of formula (I/a), a particular case of the compounds of formula (I):

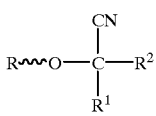
    (I/a)

wherein R, R$^1$ and R$^2$ are as defined hereinabove, or a compound of formula (VII):

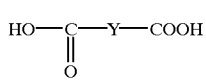
    (VII)

wherein Y is as defined hereinabove, (or the corresponding acid chloride or anhydride), to yield a compound of formula (VIII):

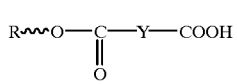
    (VIII)

wherein R and Y are as defined hereinabove, with which there is reacted under conditions of acid catalysis, in the presence of a coupling agent, or after conversion to the corresponding acid chloride, a compound of formula (VI) to obtain a compound of formula (I/b), a particular case of the compound of formula (I):

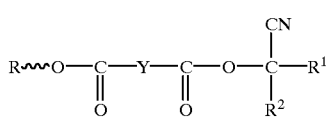
    (I/b)

wherein R, R$^1$, R$^2$ and Y are as defined hereinabove, a compound of formula (IX):

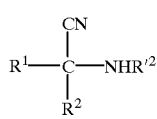
    (IX)

wherein R, R$^1$, R'$^2$ are as defined hereinabove, to yield a compound of formula (I/c), a particular case of the compounds of formula (I):

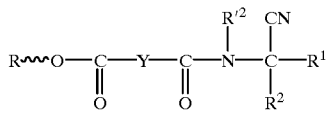
    (I/c)

wherein R, R$^1$, R$^2$, R'$^2$ are as defined hereinabove, or a compound of formula (X):

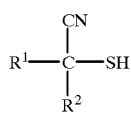
    (X)

wherein R$^1$ and R$^2$ are as defined hereinabove, to yield a compound of formula (I/d), a particular case of the compounds of formula (I):

$$R\sim O-\underset{\underset{O}{\|}}{C}-Y-\underset{\underset{O}{\|}}{C}-S-\underset{\underset{R^2}{|}}{\overset{\overset{CN}{|}}{C}}-R^1 \quad (I/d)$$

wherein R, Y, $R^1$ and $R^2$ are as defined hereinabove, which compounds (I/a) to (I/d) constitute the totality of the compounds of formula (I) and may be purified in accordance with a conventional separation technique, are converted, if desired, into their addition salts with a pharmaceutically acceptable acid or base and separated, where appropriate, into their optical or geometric isomers in accordance with conventional purification techniques.

The compound of formula (V) is readily accessible to the person skilled in the art by conventional reduction of (commercial) artemisinine. The compounds of formula (VI) are obtained by conventional condensa of a cyanide salt with the ketone of formula (XI):

$$R^1\underset{\underset{O}{\|}}{\overset{}{\diagdown}}R^2 \quad (XI)$$

wherein $R^1$ and $R^2$ are as defined hereinabove.

The compounds of formula (IX) are obtained by the action of an amine $R'^2NH_2$ wherein $R'^2$ is as defined hereinabove on the compound of formula (VI).

The compounds of formula (X) are obtained by the action of $H_2S$ in the presence of a catalyst, such as $Al_2O_3$ for example, on the compound of formula (VI).

Another advantageous process of the invention is the preparation of compounds of formula (I) in which A represents a group of formula (IV), characterised in that there is used as starting material a compound of formula (VII):

$$HO-\underset{\underset{O}{\|}}{C}-Y-COOH \quad (VII)$$

wherein Y is as defined hereinabove, (or the corresponding acid chloride or anhydride), with which there is condensed:

in the presence of a coupling agent, a compound of formula (IX):

$$R^1-\underset{\underset{R^2}{|}}{\overset{\overset{CN}{|}}{C}}-NHR'^2 \quad (IX)$$

wherein $R^1$, $R^2$ and $R'^2$ are as defined hereinabove, to yield a compound of formula (XII):

$$R^1-\underset{\underset{CN}{|}}{\overset{\overset{R^2}{|}}{C}}-\underset{\underset{|}{}}{N}-\underset{\underset{O}{\|}}{\overset{\overset{R'^2}{|}}{C}}-Y-COOH \quad (XII)$$

wherein $R^1$, $R^2$, $R'^2$ and Y are as defined hereinabove, with which there is condensed a compound of formula (V) to obtain a compound of formula (I/c), a particular case of the compounds of formula (I):

$$R\sim O-\underset{\underset{O}{\|}}{C}-Y-\underset{\underset{O}{\|}}{C}-\underset{\underset{|}{}}{\overset{\overset{R'^2}{|}}{N}}-\underset{\underset{R^2}{|}}{\overset{\overset{CN}{|}}{C}}-R^1 \quad (I/c)$$

wherein R, Y, $R^1$, $R^2$ and $R'^2$ are as defined hereinabove, a compound of formula (VI):

$$R^1-\underset{\underset{R^2}{|}}{\overset{\overset{CN}{|}}{C}}-OH \quad (VI)$$

wherein $R^1$ and $R^2$ are as defined hereinabove, to yield a compound of formula (XIII):

$$R^1-\underset{\underset{R^2}{|}}{\overset{\overset{CN}{|}}{C}}-O-\underset{\underset{O}{\|}}{C}-Y-COOH \quad (XIII)$$

wherein $R^1$, $R^2$ and Y are as defined hereinabove, with which there is condensed a compound of formula (V) to obtain a compound of formula (I/b), a particular case of the compounds of formula (I):

$$R\sim O-\underset{\underset{O}{\|}}{C}-Y-\underset{\underset{O}{\|}}{C}-O-\underset{\underset{R^2}{|}}{\overset{\overset{CN}{|}}{C}}-R^1 \quad (I/b)$$

wherein R, Y, $R^1$ and $R^2$ are as defined hereinabove, or a compound of formula (X):

$$R^1-\underset{\underset{R^2}{|}}{\overset{\overset{CN}{|}}{C}}-SH \quad (X)$$

wherein $R^1$ and $R^2$ are as defined hereinabove, to obtain a compound of formula (XIV):

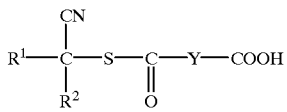
(XIV)

wherein $R^1$, $R^2$ and Y are as defined hereinabove, with which there is condensed a compound of formula (V) to obtain a compound of formula (I/d), a particu c of the compounds of formula (I):

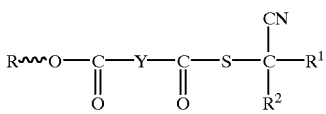
(I/d)

wherein R, Y, $R^1$ and $R^2$ are as defined hereinabove, which compounds (I/b), (I/c) and (I/d) may be purified in accordance with a conventional separation technique, are converted, if desired, into their addition salts with a pharmaceutically acceptable acid or base and are separated, where appropriate, into their optical or geometric isomers in accordance with conventional purification techniques.

The compounds of formula (I) have valuable pharmacological properties. They have excellent in vitro cytotoxicity not only on leukaemia lines but also on solid tumour lines, and they also act on the cell cycle. Those properties enable them to be used therapeutically as anti-tumour agents.

The present invention relates also to pharmaceutical compositions containing the compounds of formula (I), their optical isomers or a pharmaceutically acceptable addition salt thereof with a base or an acid, on their own or in combination with one or more inert, non-toxic excipients or carriers.

Among the pharmaceutical compositions according to the invention, there may be mentioned more especially those that are suitable for oral, parenteral, nasal, rectal, perlingual, ocular or respiratory administration, and especially tablets or dragees, sublingual tablets, sachets, paquets, gelatin capsules, glossettes, lozenges, suppositories, creams, ointments, dermal gels, injectable or drinkable preparations, aerosols, eye or nose drops.

The useful dosage varies according to the age and weight of the patient, the route of administration, the nature of the therapeutic indication and any associated treatments, and ranges from 0.1 to 400 mg per day, in one or more administrations.

The following Examples illustrate the invention and do not limit it in any way.

In the following Examples, the following nomenclature convention will be adopted:

(1R,4S,5R,9R,13S)-1,5,9-trimethyl-11,14,15-trioxatetracyclo[10.3.1.0$^{4,13}$.0$^{8,13}$]hexadec-10-yl=

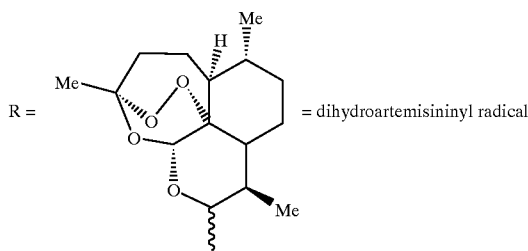
R = 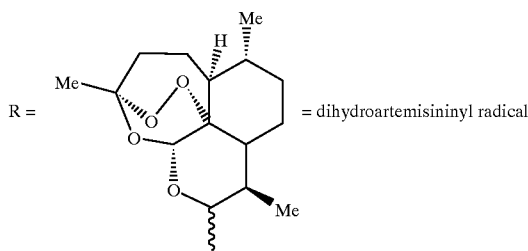 = dihydroartemisininyl radical

EXAMPLE 1

(S)-2-(4-Bromophenyl)-2-dihydroartemisininyloxy-acetonitrile

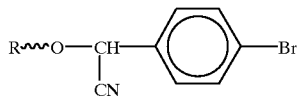

1.7 g (8 mmol) of 2-(4-bromophenyl)-2-hydroxyacetonitrile are added at −20° C. to a solution of dihydroartemisinine (1.5 g; 5.3 mmol) in 20 ml of anhydrous $CH_2Cl_2$. After the addition of $BF_3/Et_2O$ (0.1 ml; 0.8 mmol), the temperature of the solution is left to rise to room temperature again. After conventional treatment, the title compound is separated by chromatography over a silica column and then recrystallised from petroleum ether.

Melting point: 128–129°; Elemental microanalysis:

|  | C | H | N |
|---|---|---|---|
| % Calculated | 57.75 | 5.90 | 2.93 |
| % Found | 57.80 | 6.07 | 2.85 |

EXAMPLE 2

(R)-2-(4-Bromophenyl)-2-dihydroartemisininyloxy-acetonitrile

The title compound is obtained during the separation by chromatography described in Example 1.

Melting point: 144–145° C.; Elemental microanalysis:

|  | C | H | N |
|---|---|---|---|
| % Calculated | 57.75 | 5.90 | 2.93 |
| % Found | 57.52 | 5.88 | 2.65 |

EXAMPLE 3

(R)-2-(4-Fluorophenyl)-2-dihydroartemisininyloxy-acetonitrile

The procedure is the same as that used in Example 1, replacing 2-(4-bromophenyl)-2-hydroxyacetonitrile by 2-(4-fluorophenyl)-2-hydroxyacetonitrile.

Melting point: 122–125° C.; Elemental microanalysis:

|  | C | H | N |
|---|---|---|---|
| % Calculated | 66.17 | 6.76 | 3.36 |
| % Found | 66.16 | 6.74 | 3.33 |

Examples 4 to 16 are obtained by following the same procedure starting from the appropriate nitriles.

EXAMPLE 4

(S)-2-Phenyl-2-dihydroartemisininyloxy-acetonitrile

Starting materials: dihydroartemisinine and 2-phenyl-2-hydroxyacetonitrile. Melting point: 135–137° C.

EXAMPLE 5

(R)-2-Phenyl-2-dihydroartemisininyloxy-acetonitrile

Starting materials: dihydroartemisinine and 2-phenyl-2-hydroxyacetonitrile. Melting point: 98–100° C.

EXAMPLE 6

(S)-2-(3,4-Dimethoxyphenyl)-2-dihydroartemisininyloxy-acetonitrile

Starting materials: dihydroartemisinine and 2-(3,4-dimnethoxyphenyl)-2-hydroxy-acetonitrile.
Oil

EXAMPLE 7

(R)-2-(3,4-Dimethoxyphenyl)-2-dihydroartemisininyloxy-acetonitrile

Starting materials: dihydroartemisinine and 2-(3,4-dimethoxyphenyl)-2-hydroxy-acetonitrile.
Oil

EXAMPLE 8

(R)-2-(2-Fluorophenyl)-2-dihydroartemisininyloxy-acetonitrile

Starting materials: dihydroartemisinine and 2-(2-fluorophenyl)-2-hydroxyacetonitrile.
Melting point: 120–124° C.

EXAMPLE 9

(R)-2-(3-Fluorophenyl)-2-dihydroartemisininyloxy-acetonitrile

Starting materials: dihydroartemisinine and 2-(3-fluorophenyl)-2-hydroxyacetonitrile.
Melting point: 131–134° C.

EXAMPLE 10

(R)-2-(2-Bromophenyl)-2-dihydroartemisininyloxy-acetonitrile

Starting materials: dihydroartemisinine and 2-(2-bromophenyl)-2-hydroxyacetonitrile. Melting point: 128–129° C.

EXAMPLE 11

(R)-2-(3-Bromophenyl)-2-dihydroartemisininyloxy-acetonitrile

Starting materials: dihydroartemisinine and 2-(3-bromophenyl)-2-hydroxyacetonitrile. Melting point: 145–146° C.

EXAMPLE 12

(R)-2-(4-Chlorophenyl)-2-dihydroartemisininyloxy-acetonitrile

Starting materials: dihydroartemisinine and 2-(4-chlorophenyl)-2-hydroxyacetonitrile. Melting point: 142–145° C.

EXAMPLE 13

(R)-2-(2-Chlorophenyl)-2-dihydroartemisininyloxy-acetonitrile

Starting materials: dihydroartemisinine and 2-(2-chlorophenyl)-2-hydroxyacetonitrile. Meltingpoint: 137–140° C.

EXAMPLE 14

(R)-2-(3-Chlorophenyl)-2-dihydroartemisininyloxy-acetonitrile

Starting materials: dihydroartemisinine and 2-(3-chlorophenyl)-2-hydroxyacetonitrile. Melting point: 132–135° C.

EXAMPLE 15

2-(4-Nitrophenyl)-2-dihydroartemisininyloxy-propanenitrile

Starting materials: dihydroartemisinine and 2-(4-nitrophenyl)-2-hydroxy-propanenitrile.

EXAMPLE 16

[(2-Bromophenyl)(cyano)methyl] dihydroartemisininyl 1,4-succinate

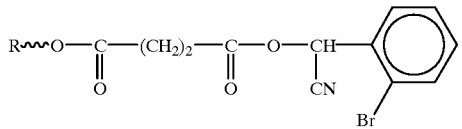

Step A: 4-Dihydroartemisininyloxy-4-oxobutanoic acid

The title product is obtained in conventional manner by condensing succinic acid or the anhydride thereof with dihydroartemisinine.

Step B: [(2-Bromophenyl)(cyano)methyl] dihydroartemisininyl 1,4-succinate 2-(2-Bromophenyl)-2-hydroxyacetonitrile (1.7 g; 8.0 mmol), DCC (1.7 g; 8.2 mmol) and DMAP (0.1 g; 0.8 mmol) are added at 0–5° C. to a solution of the compound obtained in Step A (2.0 g; 5.2 mmol) in 20 ml of $CH_2Cl_2$. The reaction mixture is stirred for 4 hours and then the white solid that has formed is filtered off. The resulting organic phase is concentrated under reduced pressure and chromatographed over a silica column (eluant: ethyl acetate/petroleum ether). The title compound is obtained in the form of a white solid.

Elemental microanalysis:

|  | C | H | N |
|---|---|---|---|
| % Calculated | 56.06 | 5.58 | 2.42 |
| % Found | 56.28 | 5.60 | 2.31 |

EXAMPLE 17

[(2-Chlorophenyl)(cyano)methyl] dihydroartemisininyl 1,4-succinate

The procedure is the same as that used in Example 16, replacing 2-(2-bromophenyl)-2-hydroxyacetonitrile in Step B by 2-(2-chlorophenyl)-2-hydroxyacetonitrile.

Elemental microanalysis:

|  | C | H | N |
|---|---|---|---|
| % Calculated | 60.73 | 6.04 | 2.62 |
| % Found | 60.91 | 6.15 | 2.69 |

Examples 18 to 27 are obtained in accordance with the same procedure, replacing 2-(2-bromophenyl)-2-hydroxyacetonitrile in Step B by the appropriate reagent.

EXAMPLE 18

[(Phenyl)(cyano)methyl]dihydroartemisininyl 1,4-succinate

Starting material: 2-phenyl-2-hydroxyacetonitrile. Melting point: 142–144° C.

EXAMPLE 19

[(4-Chlorophenyl)(cyano)methyl] dihydroartemisininyl 1,4-succinate

Starting material: 2-(4-chlorophenyl)-2-hydroxyacetonitrile

EXAMPLE 20

(1-Cyano-1-phenylethyl) dihydroartemisininyl 1,4-succinate

Starting material: 2-phenyl-2-hydroxypropanenitrile.

EXAMPLE 21

[(3,4-Dimethoxyphenyl)(cyano)methyl] dihydroartemisininyl 1,4-succinate

Starting material: 2-(3,4-dimethoxyphenyl)-2-hydroxyacetonitrile.

EXAMPLE 22

[(1,3-Benzodioxol-5-yl)(cyano)methyl] dihydroartemisininyl 1,4-suceinate

Starting material: 2-(1,3-benzodioxol-5-yl)-2-hydroxyacetonitrile.

EXAMPLE 23

[(2,4-Dimethoxyphenyl)(cyano)methyl] dihydroartemisininyl 1,4-succinate

Starting material: 2-(2,4-dimethoxyphenyl)-2-hydroxyacetonitrile.

EXAMPLE 24

[(4-Nitrophenyl)(cyano)methyl]dihydroartemisininyl 1,4-succinate

Starting material: 2-(4-nitrophenyl)-2-hydroxyacetonitrile.

EXAMPLE 25

[(4-Methoxyphenyl)(cyano)methyl] dihydroartemisininyl 1,4-succinate

Starting material: 2-(4-methoxyphenyl)-2-hydroxyacetonitrile.

EXAMPLE 26

[(4-Cyanophenyl)(cyano)methyl] dihydroartemisininyl 1,4-succinate

Starting material: 2-(4-cyanophenyl)-2-hydroxyacetonitrile.

EXAMPLE 27

{[(4-Benzyloxy-3-methoxy)phenyl][cyano] methyl}dihydroartemisininyl 1,4-succinate Starting material: 2-[(4-benzyloxy-3-methoxy)phenyl]-2-hydroxyacetonitrile.

EXAMPLE 28

[(4-Bromophenyl)(cyano)methyl] dihydroartemisininyl 1,4-succinate

Starting material: 2-(4-bromophenyl)-2-hydroxyacetonitrile.

EXAMPLE 29

[(2-Bromophenyl)(cyano)methyl] dihydroartemisininyl 1,9-azelaate

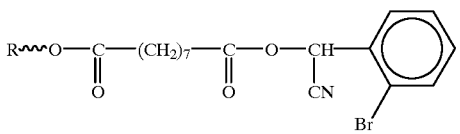

The procedure is the same as that used in Example 16, replacing succinic acid by azelaic acid in Step A.

Elemental microanalysis:

|  | C | H | N |
|---|---|---|---|
| % Calculated | 59.27 | 6.68 | 2.16 |
| % Found | 59.50 | 6.44 | 2.25 |

EXAMPLE 30

Cyano(phenyl)methyl dihydroartemisininyl 1,8-suberate

The procedure is the same as that used in Example 16, replacing succinic acid by suberic acid in Step A and replacing 2-(2-bromophenyl)-2-hydroxyacetonitrile by 2-phenyl-2-hydroxy-acetonitrile in Step B.

EXAMPLE 31

[(2-Chlorophenyl)(cyano)methyl] dihydroartemisininyl 1,6-hexanedioate

The procedure is the same as that used in Example 16, replacing succinic acid by hexanedioic acid in Step A and replacing 2-(2-bromophenyl)-2-hydroxyacetonitrile by 2-(2-chlorophenyl)-2-hydroxyacetonitrile in Step B.

EXAMPLE 32

Cyano(phenyl)methyl dihydroartemisininyl 1,2-phthalate

The procedure is the same as that used in Example 16, replacing succinic acid by phthalic acid in Step A and replacing 2-(2-bromophenyl)-2-hydroxyacetonitrile by 2-phenyl-2-hydroxyacetonitrile in Step B.

Elemental microanalysis:

|  | C | H | N |
|---|---|---|---|
| % Calculated | 68.12 | 5.90 | 2.56 |
| % Found | 68.36 | 6.06 | 2.68 |

EXAMPLE 33

Cyano-(2-bromophenyl)methyl dihydroartemisininyl 1,2-phthalate

The procedure is the same as that used in Example 16, replacing succinic acid by phthalic acid in Step A.

Meltine point: 153–155° C.

EXAMPLE 34

[(2-Chlorophenyl)(cyano)methyl] dihydroartemisininyl 1,4-(E)-2-butenedioate

The procedure is the same as that used in Example 16, replacing succinic acid by (E)-2-butenedioic acid in Step A and replacing 2-(2-bromophenyl)-2-hydroxyacetonitrile by 2-(2-chlorophenyl)-2-hydroxyacetonitrile in Step B.

EXAMPLE 35

[(2-Chlorophenyl)(cyano)methyl] dihydroartemisininyl 1,4-(2,3-dichloro)succinate The procedure is the same as that used in Exarnple 16, replacing succinic acid by 2,3-dichlorosuccinic acid in Step A and replacing 2-(2-bromophenyl)-2-hydroxyacetonitrile by 2-(2-chlorophenyl)-2-hydroxyacetonitrile in Step B.

EXAMPLE 36

[(2-Chlorophenyl)(cyano)methyl] dihydroartemisininyl 1,4-2,2-dimethylsuccinate

The procedure is the same as that used in Example 35, replacing 2,3-dichlorosuccinic acid by 2,2-dimethylsuccinic acid.

EXAMPLE 37

(Phenyl)(cyano)methyl dihydroartemisininyl 1,8-(4-bromo-1,8-naphthalene-dicarboxylate)

The procedure is the same as that used in Example 16, replacing succinic acid by 4-bromo-1,8-naphthalenedicarboxylic acid in Step A and replacing 2-(2-bromophenyl)-2-hydroxyacetonitrile by 2-phenyl-2-hydroxyacetonitrile in Step B.

EXAMPLE 38

Dihydroartemisininyl 4-{[cyano(phenyl)methyl]amino}-4-oxobutanoate

The procedure is the same as that used in Example 18, replacing 2-phenyl-2-hydroxyacetonitrile by 2-phenyl-2-aminoacetonitrile.

EXAMPLE 39

Dihydroartemisininyl 4-{[cyano-(2-chlorophenyl)methyl]amino}-4-oxobutanoate

The procedure is the same as that used in Example 17, replacing 2-(2-chlorophenyl)-2-hydroxyacetonitrile by 2-(2-chlorophenyl)-2-aminoacetonitrile.

EXAMPLE 40

Dihydroartemisininyl 4-({[cyano][(3-methoxy-4-benzyloxy)-phenyl]methyl}amino)-4-oxobutanoate The procedure is the same as that used in Example 27, replacing 2-[(3-methoxy-4-benzyloxy)phenyl]-2-hydroxyacetonitrile by 2-{(3-methoxy-4-benzyloxy)phenyl]-2-aminoacetonitrile.

EXAMPLE 41

Dihydroartemisininyl 4-{[1-cyano-1-phenylethyl]amino}-4-oxobutanoate

The procedure is the same as that used in Example 20, replacing 2-phenyl-2-hydroxy-propanenitrile by 2-phenyl-2-aminopropanenitrile.

EXAMPLE 42

Dihydroartemisininyl 4-{[cyano(phenyl)methyl][methyl]amino}-4-oxobutanoate

Step A: 2-(Methylamino)-2-phenylacetonitrile

Benzaldehyde (11 mmol) is added, with stirring, to a solution of $NaHSO_3$ (12 mmol in 4 ml of water). When a white precipitate has formed, 28 ml of an aqueous 25% methylamine solution are added dropwise, and then 12 mmol of potassium cyanide are added at 0° C. The reaction mixture is stirred at room temperature until the reaction is complete. After conventional treatment, the title product is obtained in pure form.

Step B: 4-{[Cyano(phenyl)methyl](methyl)amino}-4-oxobutanoic acid

A mixture of the compound obtained in Step A (9 mmol), succinic anhydride (7.5 mmol) and pyridine (1 ml) in methylene chloride (30 ml) is stirred overnight. After conventional treatment, the title compound is obtained in pure form.

Step C: Dihydroartemisininyl 4-{[cyano(phenyl)methyl][methyl]amino}-4-oxobutanoate A mixture of dihydroartemisinine (4.6 ml), the compound obtained in Step B (5.5 ml), DCC (6.9 mmol) and DMAP (0.2 mmol) is stirred at room temperature. At the end of the reaction, conventional treatment is carried out and the title compound is purified by chromatography over a silica column.

Melting point: 146–148° C.; Elemental microanalysis:

|  | C | H | N |
|---|---|---|---|
| % Calculated | 65.61 | 7.08 | 5.50 |
| % Found | 65.72 | 7.09 | 5.56 |

EXAMPLE 43

Dihydroartemisininyl 4-{[cyano-(4-chlorophenyl) methyl][methyl]amino}-4-oxobutanoate The procedure is the same as that used in Example 42, replacing benzaldehyde by 4-chlorobenzaldehyde.

Melting point: 142–145° C.; Elemental microanalysis:

|  | C | H | N |
|---|---|---|---|
| % Calculated | 61.48 | 6.45 | 5.12 |
| % Found | 61.55 | 6.49 | 4.90 |

EXAMPLE 44

Dihydroartemisininyl 4-{[cyano-(4-fluorophenyl) methyl][methyl]amino}-4-oxobutanoate The procedure is the same as that used in Example 42, replacing benzaldehyde by 4-fluorobenzaldehyde.

Melting point: 143–145° C.; Elemental microanalysis:

|  | C | H | N |
|---|---|---|---|
| % Calculated | 63.38 | 6.65 | 5.28 |
| % Found | 63.12 | 6.43 | 4.95 |

Examples 45 to 48 are obtained by proceeding as in Example 1, replacing 2-(4-bromophenyl)-2-hydroxyacetonitrile by the appropriate nitrile.

EXAMPLE 45

(S)-2-(2-Bromophenyl)-2-dihydroartemisininyloxy-acetonitrile

Starting materials: dihydroartemisinine and 2-(2-bromophenyl)-2-hydroxyacetonitrile; Elemental microanalysis.:

|  | C | H | N |
|---|---|---|---|
| % Calculated | 55.75 | 5.90 | 2.93 |
| % Found | 57.84 | 5.83 | 2.82 |

EXAMPLE 46

(S)-2-(3-Bromophenyl)-2-dihydroartemisininyloxy-acetonitrile

Starting materials: dihydroartemisinine and 2-(3-bromophenyl)-2-hydroxyacetonitrile; Elemental microanalysis:

|  | C | H | N |
|---|---|---|---|
| % Calculated | 57.75 | 5.90 | 2.93 |
| % Found | 57.94 | 5.92 | 2.92 |

EXAMPLE 47

(S)-2-{3-[3-(Trifluoromethyl)phenoxy]phenyl}-2-dihydroartemisininyloxy-acetonitrile Starting materials: dihydroartemisinine and 2-{3-[3-(trifluoromethyl)phenoxy]phenyl}-2-hydroxyacetonitrile; Elemental microanalysis:

|  | C | H | N |
|---|---|---|---|
| % Calculated | 64.39 | 5.76 | 2.50 |
| % Found | 64.54 | 5.81 | 2.38 |

EXAMPLE 48

(R)-2-{3-[3-(Trifluoromethyl)phenoxy]phenyl}-2-dihydroartemisininyloxy-acetonitrile Starting materials: dihydroartemisinine and 2-{3-[3-(trifluoromethyl)phenoxy]phenyl}-2-hydroxyacetonitrile; Elemental microanalysis:

|  | C | H | N |
|---|---|---|---|
| % Calculated | 64.39 | 5.76 | 2.50 |
| % Found | 64.82 | 5.97 | 2.44 |

Examples 49 to 56 are obtained by proceeding as in Example 42, replacing
in Step A, benzaldehyde by the appropriate reagent,
in Step B, succinic anhydride by the appropriate reagent.

EXAMPLE 49

Dihydroartemisininyl 4-{[(4-bromophenyl)(cyano) methyl](methyl)amino}-4-oxobutanoate Starting materials: Step A: 4-bromobenzaldehyde; Step B: succinic anhydride; Elemental microanalysis:

|  | C | H | N |
|---|---|---|---|
| % Calculated | 56.86 | 5.96 | 4.74 |
| % Found | 56.98 | 6.17 | 4.53 |

EXAMPLE 50

Dihydroartemisininyl 4-{[(cyano[phenyl]methyl) (methyl)amino]carbonyl}benzoate

Starting materials: Step A: benzaldehyde; Step B: phthalic anhydride; Elemental microanalysis.

|  | C | H | N |
|---|---|---|---|
| % Calculated | 68.56 | 6.47 | 5.00 |
| % Found | 68.37 | 6.68 | 5.23 |

EXAMPLE 51

Dihydroartemisininyl 4-{[cyano(phenyl)methyl](methyl)amino}-4-oxo-2-butenoate

Starting materials: Step A: benzaldehyde; Step B: 2-butenedioic acid; Elemental microanalysis

|  | C | H | N |
|---|---|---|---|
| % Calculated | 65.87 | 6.71 | 5.49 |
| % Found | 65.96 | 6.96 | 5.43 |

EXAMPLE 52

Dihydroartemisininyl 4-{[cyano-(2,4-dimethylphenyl)methyl](methyl)amino}-4-oxobutanoate Starting materials: Step A: 2,4-dimethylbenzaldehyde; Step B: succinic anhydride; Elemental microanalysis:

|  | C | H | N |
|---|---|---|---|
| % Calculated | 66.65 | 7.46 | 5.18 |
| % Found | 66.93 | 7.71 | 4.96 |

EXAMPLE 53

Dihydroartemisininyl 4-{[cyano-(2-fluorophenyl)methyl](methyl)amino}-4-oxobutanoate Starting materials: Step A: 2-fluorobenzaldehyde; Step B: succinic anhydride; Elemental microanalysis:

|  | C | H | N |
|---|---|---|---|
| % Calculated | 63.38 | 6.65 | 5.28 |
| % Found | 63.54 | 6.86 | 5.19 |

EXAMPLE 54

Dihydroartemisininyl 4-{[cyano-(3-fluorophenyl)methyl](methyl)amino}-4-oxobutanoate Starting materials: Step A: 3-fluorobenzaldehyde; Step B: succinic anhydride; Elemental microanalysis:

|  | C | H | N |
|---|---|---|---|
| % Calculated | 63.38 | 6.65 | 5.28 |
| % Found | 63.39 | 6.87 | 5.08 |

EXAMPLE 55

Dihydroartemisininyl 4-{[cyano-(2-bromophenyl)methyl](methyl)amino}-4-oxobutanoate Starting materials: Step A: 2-bromobenzaldehyde; Step B: succinic anhydride; Elemental microanalysis:

|  | C | H | N |
|---|---|---|---|
| % Calculated | 56.86 | 5.96 | 4.74 |
| % Found | 56.92 | 5.96 | 4.68 |

EXAMPLE 56

Dihydroartemisininyl 4-[(cyano-{3-[3-(trifluoromethyl)phenoxy]phenyl}methyl)(methyl)amino]-4-oxobutanoate Starting materials: Step A: [3-(trifluoromethyl)phenoxy]benzaldehyde; Step B: succinic anhydride; Elemental microanalysis:

|  | C | H | N |
|---|---|---|---|
| % Calculated | 62.49 | 5.84 | 4.16 |
| % Found | 62.75 | 6.08 | 3.94 |

Examples 57 to 67 are obtained by proceeding as in Example 16, replacing 2-(2-bromophenyl)-2-hydroxyacetonitrile in Step B by the appropriate acetonitrile.

EXAMPLE 57

Dihydroartemisininyl 4-{[(4-bromophenyl)(cyano)methyl]amino}-4-oxobutanoate

Starting material: 2-(4-bromophenyl)-2-aminoacetonitrile; Meltine point: 165–167° C.; Elemental microanalysis:

|  | C | H | N |
|---|---|---|---|
| % Calculated | 56.16 | 5.76 | 4.85 |
| % Found | 56.29 | 5.81 | 5.14 |

EXAMPLE 58

Dihydroartemisininyl 4-{[(4-chlorophenyl)(cyano)methyl]amino}-4-oxobutanoate

Starting material: 2-(4-chlorophenyl)-2-aminoacetonitrile; Meltine point: 164–165° C.; Elemental microanalysis:

|  | C | H | N |
|---|---|---|---|
| % Calculated | 60.84 | 6.24 | 5.25 |
| % Found | 60.86 | 6.24 | 5.43 |

EXAMPLE 59

Dihydroartemisininyl 4-{[(4-fluorophenyl)(cyano)methyl]amino}-4-oxobutanoate

Starting material: 2-(4-fluorophenyl)-2-aminoacetonitrile; Melting point: 159–162° C.; Elemental microanalysis:

|  | C | H | N |
|---|---|---|---|
| % Calculated | 62.78 | 6.44 | 5.42 |
| % Found | 62.86 | 6.49 | 5.62 |

EXAMPLE 60

Dihydroartemisininyl 4-{[(phenyl)(cyano)methyl]amino}-4-oxobutanoate

Starting material: 2-phenyl-2-aminoacetonitrile; Melting point: 153–154° C.; Elemental microanalysis:

|  | C | H | N |
|---|---|---|---|
| % Calculated | 65.04 | 6.87 | 5.62 |
| % Found | 65.20 | 6.88 | 5.69 |

EXAMPLE 61

Dihydroartemisininyl 4-{[(2-bromophenyl)(cyano)methyl]amino}-4-oxobutanoate

Starting material: 2-(2-bromophenyl)-2-aminoacetonitrile; Melting point: 156–159° C.; Elemental microanalysis:

|  | C | H | N |
|---|---|---|---|
| % Calculated | 56.16 | 5.76 | 4.85 |
| % Found | 56.31 | 5.78 | 5.11 |

EXAMPLE 62

Dihydroartemisininyl 4-{[(3-bromophenyl)(cyano)methyl]amino}-4-oxobutanoate

Starting material: 2-(3-bromophenyl)-2-aminoacetonitrile; Melting point: 153–156° C.; Elemental microanalysis:

|  | C | H | N |
|---|---|---|---|
| % Calculated | 56.16 | 5.76 | 4.85 |
| % Found | 56.17 | 5.65 | 4.71 |

EXAMPLE 63

Dihydroartemisininyl 4-{[(3-chlorophenyl)(cyano)methyl]amino}-4-oxobutanoate

Starting material: 2-(3-chlorophenyl)-2-aminoacetonitrile; Melting point: 154–156° C.; Elemental microanalysis:

|  | C | H | N |
|---|---|---|---|
| % Calculated | 60.84 | 6.24 | 5.25 |
| % Found | 60.95 | 6.02 | 5.24 |

EXAMPLE 64

Dihydroartemisininyl 4-{[(2-fluorophenyl)(cyano)methyl]amino}-4-oxobutanoate

Starting material: 2-(2-fluorophenyl)-2-aminoacetonitrile; Melting point: 161–162° C.; Elemental microanalysis:

|  | C | H | N |
|---|---|---|---|
| % Calculated | 62.78 | 6.44 | 5.42 |
| % Found | 62.91 | 6.11 | 5.31 |

EXAMPLE 65

Dihydroartemisininyl 4-{[cyano-(2-naphthyl)methyl]amino}-4-oxobutanoate

Starting material: 2-(2-naphthyl)-2-aminoacetonitrile; Melting point: 127–129° C.; Elemental microanalysis:

|  | C | H | N |
|---|---|---|---|
| % Calculated | 67.87 | 6.61 | 5.11 |
| % Found | 67.88 | 6.71 | 4.96 |

EXAMPLE 66

Dihydroartemisininyl 4-({cyano-[4-(dimethylamino)phenyl]methyl}-amino)-4-oxobutanoate Starting material: 2-[4-(dimethylamino)phenyl]-2-aminoacetonitrile; Melting point: 160–162° C.; Elemental microanalysis:

|  | C | H | N |
|---|---|---|---|
| % Calculated | 64.31 | 7.26 | 7.76 |
| % Found | 64.50 | 7.27 | 7.49 |

EXAMPLE 67

Dihydroartemisininyl 4-{[(3-fluorophenyl)(cyano)methyl]amino}-4-oxobutanoate

Starting material: 2-(3-fluorophenyl)-2-aminoacetonitrile;
Melting point: 146–148° C.; Elemental microanalysis:

|  | C | H | N |
|---|---|---|---|
| % Calculated | 62.78 | 6.44 | 5.42 |
| % Found | 62.91 | 6.11 | 5.31 |

EXAMPLE 68

Dihydroartemisininyl 4-{[cyano-(2-chlorophenyl)methyl](methyl)amino}-4-oxobutanoate The procedure is the same as that used in Example 42, replacing benzaldehyde in Step A by 2-chlorobenzaldehyde.

PHARMACOLOGICAL STUDY

The following Examples demonstrate the cytotoxic properties of the compounds of the invention and also their action on the cell cycle.

EXAMPLE A
Cytotoxicity of the Compounds

Three cell lines were used:
2 murine leukaemias: L1210, P388
1 human pulmonary carcinoma, non-small cell, A549

The cells are cultured in complete RPMI 1640 culture medium comprising 10% foetal calf serum, 2 mM glutamine, 50 units/ml of penicillin, 50 µg/ml of streptomycin and 10 Mm Hepes.

The cells are distributed on microplates and are exposed to the cytotoxic compounds. They are then incubated for the time required for cell doubling. The number of viable cells is then quantified by a colorimetric assay, the Minoculture Tetrazolium Assay (Carmichael J., De Graff W. G., Gazdar A. F., Minna J. D. and Mitchell J. R., Evaluation of a tetrazolium-based semi-automated colorimetric assay: assessment of chemosensitivity testing, Cancer Res., 47, 936–942, 1987).

The results obtained demonstrate good general cytotoxicity on the lines L1210 and P388. Moreover, it was also possible to demonstrate cytotoxic properties in respect of solid tumours, such as the line A549.

EXAMPLE B
Action on the Cell Cycle

The L1210 cells are incubated for 21 hours at 37° C. in the presence of various concentrations of test compounds. The cells are then fixed by 70% (v/v) ethanol, washed twice in PBS and incubated for 30 minutes at 20° C. in PBS that contains 100 µg/ml of RNAse and 50 µg/ml of propidium iodide. The percentage in the G2+M phase is calculated and the results are expressed according to a classification determined in terms of the percentage of the cells that accumulate in the G2+M phase after 21 hours, compared with the control (control: 20%). The compounds of the invention exhibit an accumulation of more than 60% of cells in the G2+M phase after 21 hours for concentrations of compounds ranging from 0.5 to 50 µM.

Moreover, the compounds of the invention exhibit an induction of apoptosis at cytotoxic doses.

EXAMPLE C
Tablets Each Comprising 10 mg of (R)-2-(4-bromophenyl)-2-dihydroartemisininyl-acetonitrile

| Formulation for the preparation of 1000 tablets | |
|---|---|
| (R)-2-(4-bromophenyl)-2-dihydroartemisininyl-acetonitrile | 10 g |
| Wheat starch | 15 g |
| Maize starch | 15 g |
| Lactose | 65 g |
| Magnesium stearate | 2 g |
| Silica | 1 g |
| Hydroxypropyl cellulose | 2 g |

We claim:
1. A compound selated from those of formula (I):

R—O—A    (I)

wherein:
R represents the radical of formula (II):

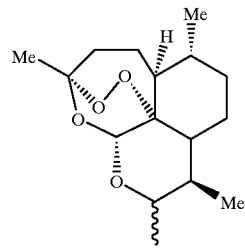

(II)

A represents:
a group of formula (III):

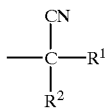

(III)

wherein—$R^1$ represents aryl, substituted aryl, heteroaryl or substituted heteroaryl,
—$R^2$ represents hydrogen or substituted or unsubstituted linear or branched $(C_1–C_6)$alkyl,
or a group of formula (IV):

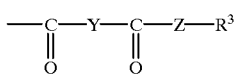

(IV)

wherein—Y represents substituted or unsubstituted linear or branched $(C_2–C_{14})$alkylene, substituted or unsubstituted linear or branched $(C_2–C_{14})$ alkenylene, substituted or unsubstituted linear or branched ($C_2$–$C_{14}$)alkynylene, phenylene, substituted phenylene, naphthylene or substituted naphthylene, —Z represents oxygen or sulphur, or $NR'^2$ wherein $R'^2$ can have the same meanings as $R^2$, —$R^3$ represents a group of formula (III) as defined hereinabove, it being understood that:

"aryl" is understood to mean phenyl, naphthyl, phenanthryl, fluorenyl or anthryl, "heteroaryl" is understood to mean any mono- or bi-cyclic aromatic group containing from 5 to 10 atoms and which may contain from 1 to 3 hetero atoms selected from oxygen, nitrogen and sulphur, the term "substituted" applied to the terms "aryl", "heteroaryl", "phenylene" and "naphthylene" means that those groups are substituted by one or more identical or different radicals selected from linear or branched ($C_1$–$C_6$)alkyl, hydroxy, linear or branched ($C_1$–$C_6$)alkoxy, ($C_1$–$C_6$)alkoxycarbonyl, polyhalo-($C_1$–$C_6$)alkyl in which the alkyl moiety is linear or branched, aryloxy (unsubstituted or substituted by one or more identical or different groups selected from hydroxy, linear or branched ($C_1$–$C_6$)alkyl, linear or branched ($C_1$–$C_6$)-alkoxy, polyhalo-($C_1$–$C_6$)alkyl in which the alkyl moiety is linear or branched, and halogen), nitro, amino, linear or branched ($C_1$–$C_6$) alkylamino, di-($C_1$–$C_6$)alkylamino in which each alkyl moiety is linear or branched, alkylcarbonylamino, cyano and halogen (fluorine, chlorine, bromine or iodine), or two adjacent carbon atoms may be substituted by alkylenedioxy, the term "substituted" applied to the terms "alkyl", "alkylene", "alkenylene" and "alkynylene" means that those groups are substituted by one or more identical or different radicals selected from hydroxy, linear or branched ($C_1$–$C_6$)alkoxy, polyhaloalkyl, amino and halogen (fluorine, chlorine, bromine or iodine), its enantiomers and diastereoisomers, and addition salts thereof with a pharmaceutically acceptable acid or base.

2. A compound of claim 1 wherein A represents a group of formula (III).

3. A compound of claim 1 wherein A represents a group of formula (IV).

4. A compound of claim 1 wherein Z represents oxygen.

5. A compound of claim 1 wherein Z represents $NR'^2$.

6. A compound of claim 1 wherein Y represents a ($C_2$–$C_{14}$)alkylene or ($C_2$–$C_{14}$)alkenylene chain, each substituted or unsubstituted.

7. A compound of claim 1 wherein Y represents phenylene or naphthylene, each substituted or unsubstituted.

8. A compound of claim 1 wherein $R^1$ represents aryl or substituted aryl.

9. A compound of claim 1 selected from 2-(4-bromophenyl)-2-dihydroartemisininyl-acetonitrile, its enantiomers and diastereoisomers ((R)-2-(4-bromophenyl)-2-dihydroartemisininyl-acetonitrile and (S)-2-(4-bromophenyl)-2-dihydroartemisininyl-acetonitrile)), and addition salts thereof with a pharmaceutically acceptable acid or base.

10. A compound of claim 1 selected from 2-phenyl-2-dihydroartemisininyl-acetonitrile, its enantiomers and diastereoisomers ((R)-2-phenyl-2-dihydroartemisininyl-acetonitrile and (S)-2-phenyl-2-dihydroartemisininyl-acetonitrile)), and addition salts thereof with a pharmaceutically acceptable acid or base.

11. A compound of claim 1 selected from [(2-chlorophenyl)(cyano)methyl]dihydroartemisininyl 1,4-succinate, its enantiomers and diastereoisomers ((R)-[(2-chlorophenyl)(cyano)methyl]dihydroartemisininyl 1,4-succinate and [(S)-(2-chlorophenyl)(cyano)methyl] dihydroartemisininyl) 1,4-succinate), and addition salts thereof with a pharmaceutically acceptable acid or base.

12. A compound of claim 1 selected from dihydroartemisininyl 4-{[(4-bromophenyl)(cyano)methyl](methyl) amino)}4-oxobutanoate, its enantiomers and diastereoisomers ((R)-dihydroartemisininyl 4-{[(4-bromophenyl)(cyano)methyl](methyl)-amino}-4-oxobutanoate and (S)-dihydroartemisininyl 4-{[(4-bromophenyl)(cyano)methyl]-(methyl) amino}-4-oxobutanoate), and addition salts thereof with a pharmaceutically acceptable acid or base.

13. A method for treating a living animal body afflicted with cancer comprising the step of administering to the living body an amount of a compound of claim 1 which is effective for treating cancer.

14. A pharmaceutical composition useful for treating cancer comprising, as active principle an effective amount of a compound as claimed in claim 1, together with one or more pharmaceutically acceptable excipients or vehicles.

* * * * *

UNITED STATES PATENT AND TRADEMARK OFFICE
CERTIFICATE OF CORRECTION

PATENT NO. : 6,307,068 B1  Page 1 of 1
DATED : October 23, 2001
INVENTOR(S) : Ying Li et al.

It is certified that error appears in the above-identified patent and that said Letters Patent is hereby corrected as shown below:

Column 22,
Line 25, "selated" should read -- selected --.

Column 24,
Line 24, "amino)}" should read -- amino}, --.

Signed and Sealed this

Twenty-eighth Day of January, 2003

JAMES E. ROGAN
*Director of the United States Patent and Trademark Office*